United States Patent
Schoen (10) Patent No.: US 9,968,322 B2
(45) Date of Patent: May 15, 2018

(54) METHOD FOR EARLY RECOGNITION OF BONE AND JOINT DISEASES

(71) Applicant: BRAINCON Handels-GmbH, Vienna (AT)

(72) Inventor: Christian Schoen, Vienna (AT)

(73) Assignee: Braincon Handels-GMBH, Vienna (AT)

(*) Notice: Subject to any disclaimer, the term of this patent is extended or adjusted under 35 U.S.C. 154(b) by 0 days. days.

(21) Appl. No.: 15/038,006

(22) PCT Filed: Nov. 28, 2014

(86) PCT No.: PCT/AT2014/050285
§ 371 (c)(1),
(2) Date: May 19, 2016

(87) PCT Pub. No.: WO2015/077813
PCT Pub. Date: Jun. 4, 2015

(65) Prior Publication Data
US 2016/0302749 A1    Oct. 20, 2016

(30) Foreign Application Priority Data
Nov. 29, 2013 (AT) .................................. A 921/2013

(51) Int. Cl.
*G06K 9/00* (2006.01)
*A61B 6/00* (2006.01)

(52) U.S. Cl.
CPC ............ *A61B 6/505* (2013.01); *A61B 6/5217* (2013.01)

(58) Field of Classification Search
CPC ......... A61B 6/505; A61B 6/5217; A61B 6/14; A61B 8/5223; A61B 8/52; A61B 5/4509; A61B 5/748; A61B 5/7275; A61B 5/055; G06T 2207/30008; G06T 2207/10081; G06T 2207/20021
See application file for complete search history.

(56) References Cited

U.S. PATENT DOCUMENTS

| | | | |
|---|---|---|---|
| 9,460,506 B2* | 10/2016 | Arnaud | G06T 7/0012 |
| 2007/0047794 A1* | 3/2007 | Lang | G06T 7/0012 |
| | | | 382/132 |
| 2010/0145231 A1 | 6/2010 | Takahashi et al. | |

(Continued)

FOREIGN PATENT DOCUMENTS

WO    2010033210 A2    3/2010

OTHER PUBLICATIONS

Austrian Search Report, Application No. A 921/2013, dated Jun. 12, 2014, 1 page.

(Continued)

*Primary Examiner* — Ali Bayat
(74) *Attorney, Agent, or Firm* — Hoffmann and Baron LLP (57) ABSTRACT

A method for early recognition of bone and joint diseases, such as osteoarthritis, by radiographic analysis, in which a digital radiographic image of the bone in the area of the joint head and/or joint socket is taken and the fractal dimension of at least one image zone is determined, and a bone structural value is calculated on the basis of the fractal dimension of the at least one image zone and used for assessing the state of health of the joint is disclosed.

11 Claims, 7 Drawing Sheets

(56) References Cited

U.S. PATENT DOCUMENTS

| | | | |
|---|---|---|---|
| 2010/0303358 A1* | 12/2010 | Acharyya | A61B 5/7264 |
| | | | 382/190 |
| 2012/0114211 A1 | 5/2012 | Kraus et al. | |
| 2014/0126800 A1* | 5/2014 | Lang | A61B 6/505 |
| | | | 382/132 |
| 2016/0253797 A1* | 9/2016 | Lang | A61B 6/469 |
| | | | 382/132 |

OTHER PUBLICATIONS

Majumdar, et al., "Fractal Analysis of Radiographs: Assessment of Trabecular Bone Structure and Prediction of Elastic Modulus and Strength", Med. Phys. pp. 1330-1340, Jul. 26, 1999.
Messent, et al., "Tibial Cancellous Bone Changes in Patients with Knee Osteoarthritis. A Short-Term Longitudinal Study Using Fractal Signature Analsysis", OsteoArthritis and Cartilage, pp. 463-470, vol. 13, Jul. 1, 2004.
Wolski, et al., "Directional Fractal Signature Analysis of Trabecular Bone: Evaluation of Different Methods to Detect Early Osteoarthritis in Knee Radiographs", Proc. IMechE, vol. 223 Part H: J. Engineering in Medicine, pp. 211-236, Apr. 10, 2008.
International Search Report, Application No. PCT/AT2014/050285, dated Mar. 17, 2015.
International Preliminary Report on Patentability, Application No. PCT/AT2014/050285, dated Jun. 16, 2016.

* cited by examiner

METHOD FOR EARLY RECOGNITION OF BONE AND JOINT DISEASES

CROSS-REFERENCE TO RELATED APPLICATIONS

This application is a National Stage application of International Application No. PCT/AT2014/050285, filed Nov. 28, 2014, which claims priority to Austrian Application No. A921/2013, filed Nov. 29, 2013, which are incorporated by reference herein in their entireties.

BACKGROUND

Field

The invention relates to a method for the early detection of bone joint diseases such as osteoarthritis by X-ray analysis.

Related Art

There have been efforts for some time in preventive medicine to detect and treat the effects of joint diseases at an early stage.

A bone joint includes a joint head and a socket, which are formed by bones, while it is also possible to refer to them as two joint heads.

Due to the cancellous bone tissue (also referred to as trabecular structure) with its microscopic support structures, the bone structure is in general both lightweight and highly resistant to tensile, compressive, torsional and bending loads. Factors such as age, poor diet and lack of exercise can deteriorate the tissue over time, and the support structures will degrade.

Osteoarthritis, for example, is the most common disease of the human joint as well as a common cause for disabilities and pain in the locomotor system. Osteoarthritis (OA) is particularly common among a considerable share of the population aged 50+ and in particular among women.

Rheumatoid arthritis is a joint inflammation and affects mostly persons aged between 40 and 60. Women are affected three times as often as men. The reasons are largely unknown, but certain environmental factors play an important role in the course of the inflammation process. A tumor-like tissue ("pannus") having a cartilage-damaging effect is formed due to the immigration of defence cells (leukocytes) into the inflamed region. Often affected joints are the finger joints, elbow joints and knee joints. As a consequence of cartilage damage, bone tissue may chafe other bone tissue directly, as the buffer effect of the cartilage is no longer active.

A diagnosis found as soon as possible is an enormously important factor in the prognosis of these diseases, as timely treatment with medicaments may slow down or even stop joint damage.

Despite their effects of society, there is a lack of information about the factors that allow the disease to progress faster in some individuals than in others. While osteoarthritis was previously considered a degenerative "wear-related" disease allowing few chances of therapeutic intervention, it is today increasingly regarded as a dynamic process with potential for novel pharmacological and surgical treatment modalities such as cartilage transplantation, chondral allo- or auto-grafting, osteotomies and tibial corticotomies with square-shaped distraction.

The respective provision and selection of treatment interventions for OA, however, relies on the development of improved methods of assessing the state of the joints and the bone degeneration in a patient.

There is therefore a need for improved non-invasive methods for testing factors and quantifying disease progression and for early detection.

The general picture is similar in the field of rheumatoid arthritis. While the prevalence is markedly smaller, the costs for governments and those affected are relatively higher.

In known methods, in which a mere bone density measurement is undertaken, changes in the bone condition often do not show before a phase in which the joint disease has already progressed.

SUMMARY

It is a task of the invention to indicate a method for the early detection of bone joint diseases which can be performed at a small expense of time and equipment while at the same time helping detect changes in the internal bone structure at an early point in time.

According to the invention, this is achieved by taking a digital radiograph of the bone in the area of the joint head and/or the socket and determining the fractal dimension of at least one image region, and by calculating, based on said fractal dimension of said at least one image region, a bone structure value that can be used to assess the joint disease state.

The inventive method performs a fractal analysis of the grey levels of a selectable image region (ROI—region of interest) in a radiograph of the area around the joint head and/or the socket to measure the bone structure in order to determine the BSV (bone structure value) based on the fractal dimension. The changes in the grey levels in horizontal and vertical directions reveal the quality of the bone microarchitecture. Each selected region of interest provides a value between zero and one, with one representing the optimum bone and zero the poorest possible bone.

The decisive factor here is the correlation between the bone condition in a selected range of interest in the area around the joint head and/or the socket and a budding joint disease. If certain bone structure conditions are present, preventive and/or prophylactic measures may be taken to prevent the disease from progressing.

The starting point is a radiograph with a resolution of e.g. <200 μm pixel size. After defining the image region of interest, the algorithm begins evaluating the changes in grey levels pixel line by pixel line, in which the various grey levels ultimately reveal how thick the trabecular structure is at each respective site and whether or not it is continuous. When the entire image region is analysed, the grey-level curves of the individual lines are averaged and transferred into the fractal dimension by fractal analysis using the Brownian motion. It is a two-dimensional construct which also contains information from the third dimension. The BSV value is then determined from said dimension.

However, the invention is not limited to the mathematical method of calculation described above, but other methods of calculation may also be used to determine the fractal dimension of the grey levels.

According to another embodiment of the invention, multiple image regions are analysed, in which the recorded digital radiograph is divided into multiple grid areas by an analysis grid, each grid area forming one of the image regions, and the analysis grid consisting of at least one line and at least two columns.

The matrix-like arrangement of the image regions to be evaluated allows simple calculation pixel line by pixel line, with the division being made by an analysis grid or equivalent subdivisions using digital processing of the image data obtained from the digital radiograph.

Based on this subdivision into multiple image regions, evaluations can be made with regard to which of the image regions contribute the most to a distinction between diseased and healthy bone joints, thereby helping improve early detection.

Thus, according to an advancement of the invention, for each grid area, the fractal dimension can be determined pixel line by pixel line for each image pixel contained therein, and selected grid areas can be used to assess the joint disease condition.

In order to obtain more information on the selected image area or the selected image area itself, the direction of calculation is mostly rotated a certain angle, the calculation is repeated and the results are then averaged. The number of directions from which the calculation is made can also be freely chosen, but it is uncommon to use more than eight. The reason for these methods is that the trabeculae are easier to spot from certain directions than from others.

It has been found to be preferable—without being limited thereto—to select the analysis grid such that it has 1 to 3 lines and 3 to 8 columns.

Another variant of the invention may be to determine the fractal profile as a radial distribution of the fractal dimensions of a grid line.

According to another embodiment of the invention, radiographs taken in evaluation intervals may be used to assess the course of the disease and a change rate and progression factors may be determined based on the same.

Further, the analysis data can be collected for the fractal dimension of a larger group of examined patients and related to sex, age, ethnicity, weight, height or the like to determine standard curves.

According to a preferred embodiment of the invention, a digital detector with a grid resolution of less than 200 μm may be used for the x-ray exposure.

The inventive procedure may be used to assess the condition of all bone joints, for example, a knee joint, a hip joint, a hand joint or the like may be assessed.

For the assessment of a knee joint, for example, the analysis grid may be arranged in the area of the tibial head in the recorded digital radiograph, with the full width of the analysis grid equalling 60 to 100% of the width of the tibial plateau, the full height of the analysis grid being from 5% to 60% of the width of the tibial plateau and the top edge of the analysis grid being potentially arranged between 0 and 20 mm below the cortical bone of the tibial plateau depicted in the radiograph.

According to another advantageous advancement of the invention, the analysis grid may be arranged symmetrically with respect to the central axis of the tibia depicted in the radiograph and parallel to the medial and lateral tibial plateau depicted. Highly diagnostic grid areas and image regions may be obtained based on this arrangement of the analysis grid.

For other joints, the arrangement of the analysis grid may be adapted according to requirements.

For all measurements undertaken in the course of the invention, a preferably high reproducibility of the joint position relative to the x-ray is desired.

A measure for achieving this goal may be, for example, to record the digital radiograph of the knee joint region while standing and being subjected to a weight load.

It has further been found advantageous if the x-ray beam, according to a preferred embodiment, is allowed to enter on the knee pit side and exit on the kneecap side when recording the digital radiograph (back-to-front position), where it impinges upon a detector.

For the application of the inventive method it has further been found advantageous if, according to another variant of the invention, the tibial axis is kept tilted with respect to a vertical direction by an adjustable angle θ of preferably 5 to 20° during the recording of the digital radiograph, such that the axis of the x-ray runs essentially parallel to the tibial plateau. This way, the tibial plateau is brought into a parallel position with respect to the x-ray, resulting in very low interferences for the determination of the grey levels of the selected image regions.

In order to determine the joint disease condition according to an embodiment of the invention, an assessment of the joint space is further conducted by measuring a joint space area.

The quality of the bone microarchitecture can thus be used in combination with an improved assessment of the joint space to allow assessment of bone joint diseases such as osteoarthritis. Significance regarding the overall bone condition is markedly improved, early detection is made possible, time course analyses are improved and the fracture risk can be determined more accurately.

The method applied according to this variant of the invention to measure the joint space provides a markedly improved analysis of the joint space width. Measurement ranges whose dimensions are related to anatomically set distances are placed above the joint space in certain areas and measure the joint space area instead of only determining the height. To be able to achieve this, it is necessary to know the position of the bone contours. For this reason, the measures for orienting and fixating the bone joints during the x-ray exposure described above are also applied.

The ratio of the entire measurement range area and the measured joint space area provides a value that reflects the joint space very accurately and reacts sensitively to changes in the case of repeated measurements. In addition, the minimum height in the joint space is determined and indicated. In order to achieve this measurement accuracy in the case of the recording as well, a knee position must be used as mentioned above. It will provide for the knee being adjustably fixated during the recordings, which will result in high accuracy and reproducibility.

The developed analysis of the joint space area is based on the finding that previous methods use manually marked distances between the bone heads. Manual inaccuracies, poor and inconsistent recording positions and/or inadequate image qualities are largely disregarded. The drawbacks mentioned are eliminated according to another embodiment of the invention by the following steps:

recognising or generating the contours of the bone heads of the joint;

marking vertices of the bone heads;

defining at least one measurement range covering the joint space between the marked vertices, which has a width smaller than the joint head width and dimensions related to the joint head width;

measuring the joint space area within the at least one measurement range;

determining the ratio of the area of the at least one measurement range and the joint space area present within the at least one measurement range.

During the recording, the respective body region should be fixated in a repeatable manner. This defines the perspective of the recording permanently. For example, the knee recording is preferably done in back-to-front direction. The patella directly abuts the detector during the recording in order to achieve minimum enhancement and scattering. The x-ray beam is gauged to the knee pit. With the human tibial plateau having an inclination of 0-20°, the lower leg is also inclined during the recording by an adjustable angle (of typically 10°).

The image quality is secured by fixed requirements and the distance measurement is extended to become an area measurement. This is only possible if information on the bone contour positions is available. If it is, the joint space area in certain regions of the joint space can be determined. Typically, one will take those regions passed through by the main load. In order to make the measurements comparable for different joint sizes, geometrical elements are used as measurement ranges, the sizes of which depend on set anatomical dimensions. In addition, the ratio of the area of the geometrical elements and the joint space areas is formed. This reveals an area quotient that is between zero and one and therefore remains comparable and lucid. Measurement of the joint space as an area increases the sensitivity and accuracy of the procedure. The actual benefit of this method results from a progress control function. Starting from the second measurement, the current values are supposed to be compared to the previous values and the percent change documented. As a reference, the first and the next to last measurement may be used.

According to another embodiment of the invention, the medial and lateral area quotient of the area from the medial and lateral joint spaces between tibia and femur and the surrounding measurement ranges may be determined to assess the joint space of a knee joint, the width of the measurement ranges being between 5% and 45% of the tibial width and an indentation of 2 to 15% being made on both sides of the tibial width.

According to another exemplary embodiment of the invention, the heights of the medial or lateral joint space between tibia and femur may be determined at multiple sites within a lateral and a medial measurement range, respectively, being between 5% and 45% of the tibial width and having an indentation of 2 to 15% on both sides of the tibial width.

Finally, it has proven advantageous when an evaluated combination of values of the fractal dimension from various analysis grid areas, the joint space heights and the quotients of the joint space area is used to assess the joint disease condition.

BRIEF DESCRIPTION OF THE DRAWINGS

The invention will be explained in detail referring to the exemplary embodiments illustrated in the drawings, in which.

DETAILED DESCRIPTION

Figure 1:
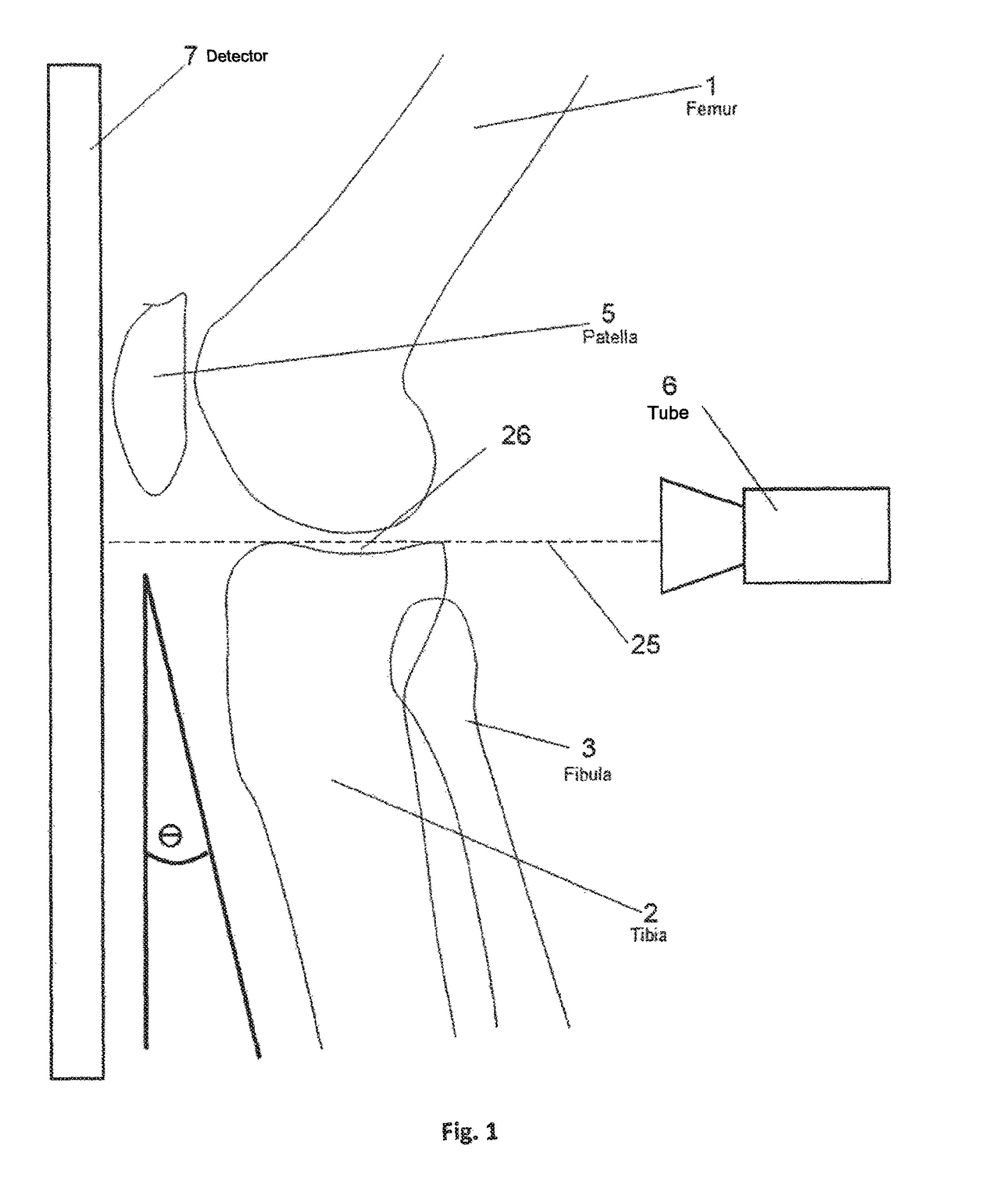
FIG. 1 shows a schematic side view of a knee joint with a digital x-ray apparatus for executing an embodiment of the method according to the invention.

FIG. 1 shows an arrangement to record a digital radiograph with an x-ray tube 6 and a detector 7, which transforms an x-ray 25 attenuated while passing through a joint region into a digital image. A knee joint is illustrated to explain the application of the method according to the invention in an exemplary manner, however, any other joint of the human body could be analysed as shown.

In FIG. 1, the most important bones of the knee joint are shown: a femur 1, a tibia 2, a fibula 3 and a patella 5, while cartilage and tendon masses are not depicted for the sake of clarity.

For the recording of the digital radiograph, the x-ray beam 25 will enter on the knee-pit side and exit one the kneecap side (back-to-front position), where it will impinge on the detector 7.

During the recording, it is preferred that the respective body region is fixated in a repeatable manner. This defines the perspective of the recording permanently. For example, the knee recording in FIG. 1 is preferably done in back-to-front direction. The patella 5 directly abuts the detector 7 during the recording in order to achieve minimum enhancement and scattering.

The x-ray 25 is gauged to the knee pit. With the human tibial plateau having an inclination of 0-20°, the lower leg is also inclined during the recording by an adjustable angle θ of preferably 5 to 20° and typically 10°, such that the axis of the x-ray 25 is essentially parallel to the tibial plateau 26, which has a slightly curved shape. The adjustability of the angle θ allows accounting for individual differences in bone shape.

According to the invention, a digital radiograph of the bone is recorded in the bone head region and/or the socket and the fractal dimension of at least one image region is determined, whereby a bone structure value is calculated based on the fractal dimension of the at least one image region, which is then used to assess the joint disease condition.

Figure 2:
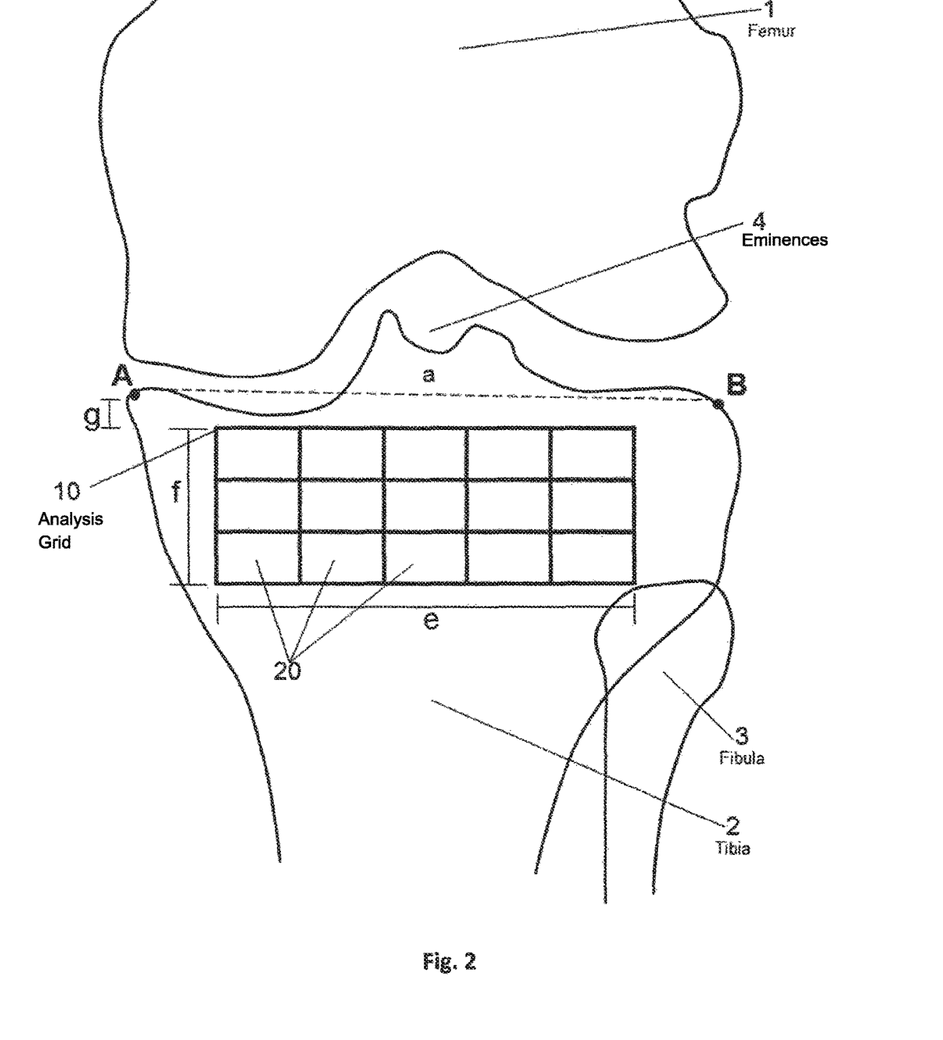
FIG. 2 shows a schematic rear view of a radiograph of a knee joint with an added analysis grid for executing another embodiment of the method according to the invention.

FIG. 2 schematically shows a digital radiograph of a knee joint taken using the arrangement shown in FIG. 1.

The recorded digital radiograph is subdivided into grid areas 20 by an analysis grid 10, which analysis grid 10 is made up of at least one line and at least two columns. In the exemplary embodiment shown, three lines and five columns are provided.

The fractal value for each grid area 20 is determined pixel line by pixel line for the grey levels of the image pixels contained therein, and selected grid areas 20 are used to assess the disease condition.

In each grid area 20 of the analysis grid 10, a fractal analysis of the grey levels of this ROI (region of interest) is first made in order to determine a bone structure value (BSV) via the fractal dimension to be able to derive the disease condition of the joint from said BSV.

The change of grey levels within each pixel line (horizontal) and each pixel column (vertical) reveal the quality of the microarchitecture. A value between zero and one is obtained for each grid area 20, with one representing the optimum and zero the worst possible bone.

A known fractal algorithm is used to calculate the fractal dimension of the grid areas 20. It is based on the Brownian motion model or, more precisely, on the fractional Gaussian noise (FGN) based on the definition of a stochastic integral in the frequency domain $$B_H(t) = \frac{1}{2\pi} \int_{-\infty}^{+\infty} \frac{1}{(i\omega)^{H+1/2}} (e^{it\omega} - 1) dB(\omega)$$

The application of said model is considered validated when two conditions are met, i.e. the Gaussian distribution and the self-similarity of the data. As these conditions are typically present in digital radiographs, the model is well suited for the algorithm and the methods described herein.

It needed to be examined how the algorithm behaves under certain circumstances and in certain areas. Evaluations revealed that the isolated factors "size" and "proportion" have a very minor effect on the BSV. Scattered rays appear to have a larger influence on the region beneath the eminences 4. For this reason and because of the anatomic geometry (smaller fluoroscopic distance), the BSV of the lateral regions represents the bone condition best. As the cortical bone (bone cortex) has a distorting effect on the BSV, the selected grid areas 20 (ROIs) should be placed a few millimetres (g) beneath the edge of the tibial plateau. It has been shown that women have much smaller values than men. A critical factor for a deterioration of the bone condition seems to be the BMI. Age has a much smaller but still discernible effect.

The analyses have also shown that the medial region (joint interior) exhibits higher values than the lateral region (joint exterior).

Also, an evaluation matrix was created for the image regions 20, which indicates for a certain individual test cohort how much significance (0-100%) the individual image regions 20 bear with respect to the assessment.

FIG. 2 shows a potential embodiment of the application of the method according to the invention, in which marks A, B corresponding to exterior points of the tibial plateau in essentially horizontal orientation of the same are first set to then place an analysis grid 10 over the tibial joint head. The grid has preferably one to three lines and 2 to 10 columns. In the exemplary embodiment shown, there are three lines and five columns.

The entire grid has a width e of 60 to 100% and a height f of 10 to 60% of the tibial head width a.

The grid generally places itself parallel to line a and exactly between points A and B, its top edge, however, being 0 to 20 mm, but typically 8 mm, below the lowest contours, more precisely the cortical bone, of the tibial plateau.

The analysis grid is preferably symmetrical with respect to the central axis of the tibia 2.

To generate a mean value, the analysis grid may be rotated around an angle α n times, until a 360° rotation is achieved and the fractal dimension is calculated after each rotation.

This embodiment of the method according to the invention is based on the fractal dimension being determined in multiple directions of a region of interest by means of rotation. In each direction, line after line is evaluated and centred. The Brownian motion model or the FGN is applied. The mathematical model is based on statistical data.

The mean value is formed from the fractal dimensions of each ROI 20 as determined by rotation. The result of this calculation is between 0 and 1.

The course of the fractal dimension in the matrix elements is further determined. It helps determine a profile of the fractal dimension over the cross section, which may then be used for further diagnostic findings.

The method described in WO20100333210 pursues a different approach. In this method, within (only) one region of interest, the fractal dimension curves are determined only in the X and Y axes of said region of interest using fractal signal analysis (FSA). Fractal analyses are performed in vertical and horizontal directions. Indirectly, this also provides a result for the trabeculae sizes. Progresses in horizontal and vertical directions are referred to as fractal dimension curves, which are further converted into a "statistical model" using a polynomic regression.

Figure 6:
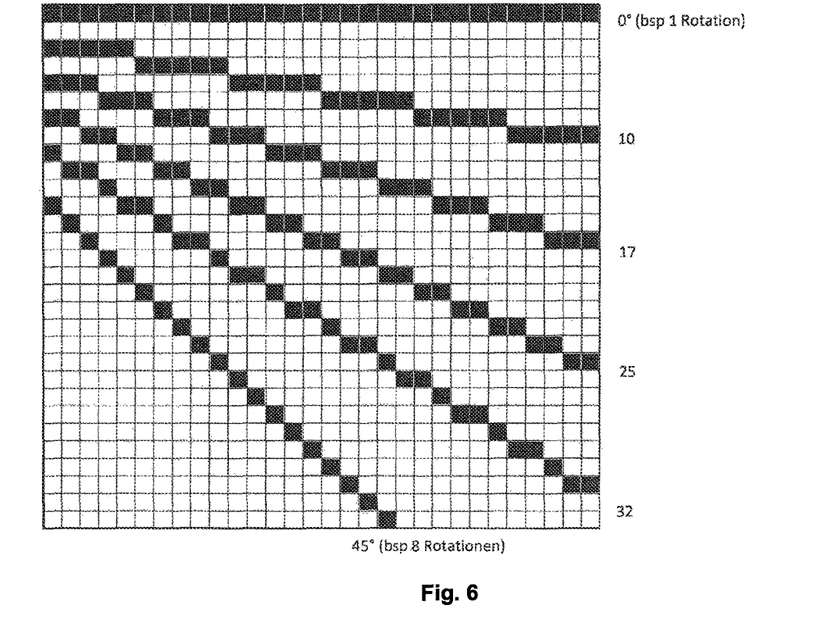
FIG. 6 shows a graph with different rotated line series from a pixel grid.

In the method according to the invention, the rotations of the regions of interest 20 are applied, as difficulties occur in fractal analyses when quantification of the bone microstructure and anisotropy is performed on different scales. Fractal methods are only able to calculate the bone structure in vertical and horizontal directions. Several studies have demonstrated, however, that OA-related changes in bone structure may occur in any direction. In order to overcome this issue, the region of interest 20 is rotated as follows to subsequently extract line series from the pixel grid to supply them to the actual analysis (FIG. 6). If desired, the rotations may be increased to allow for an analysis from various directions. In practice, a number between 4 and 8 rotations has shown to be suitable.

Figure 5:
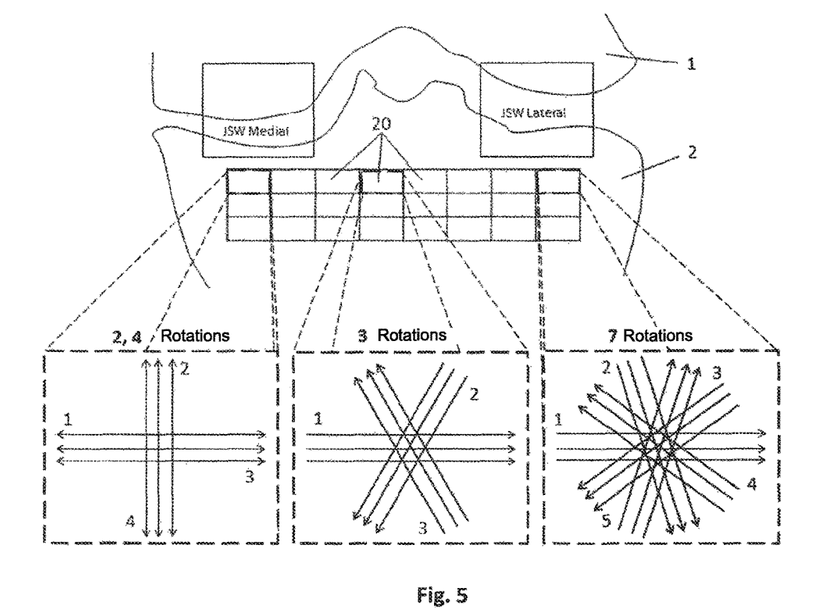
FIG. 5 shows a schematic rear view of a radiograph of a knee joint with an added analysis grid for executing another embodiment of the method according to the invention.

FIG. 5 shows the selection of lines in various directions from the pixel grid. The selection of lines in the direction of the pixel grid main axes is unambiguous. If the lines are inclined towards the main grid, the selection is made based on the aspect that the respective pixel is selected along the line the analysis axis passes through.

Figure 7:
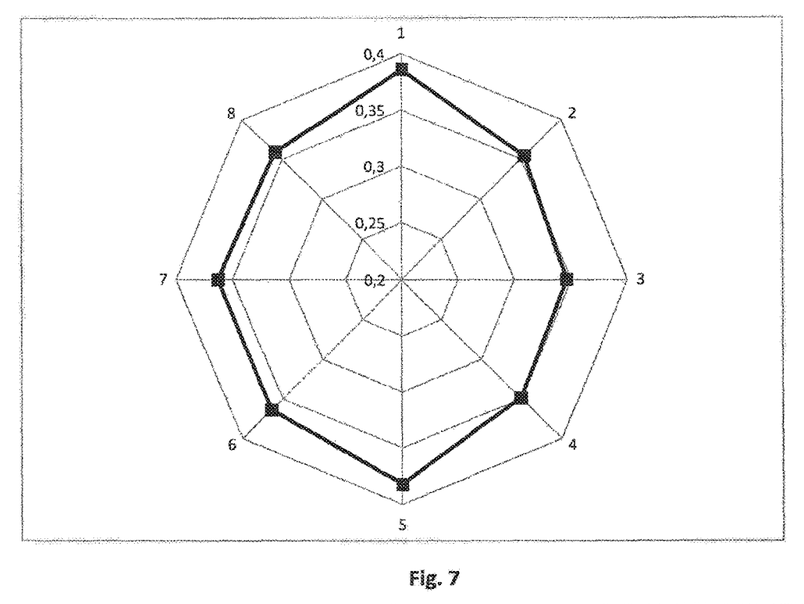
FIG. 7 shows a graph of the bone structure value over the ROI rotation angle.

For example, according to table 1 and FIG. 7, a calculation including 8 rotations will provide the following:

TABLE 1

| | Angle of rotation | BSV |
|---|---|---|
| 1 | 0 | 0.386 |
| 2 | 45 | 0.354 |
| 3 | 90 | 0.346 |
| 4 | 135 | 0.349 |
| 5 | 180 | 0.382 |
| 6 | 225 | 0.364 |
| 7 | 270 | 0.363 |
| 8 | 315 | 0.359 |

BSV medium: 0.363

Figure 8:
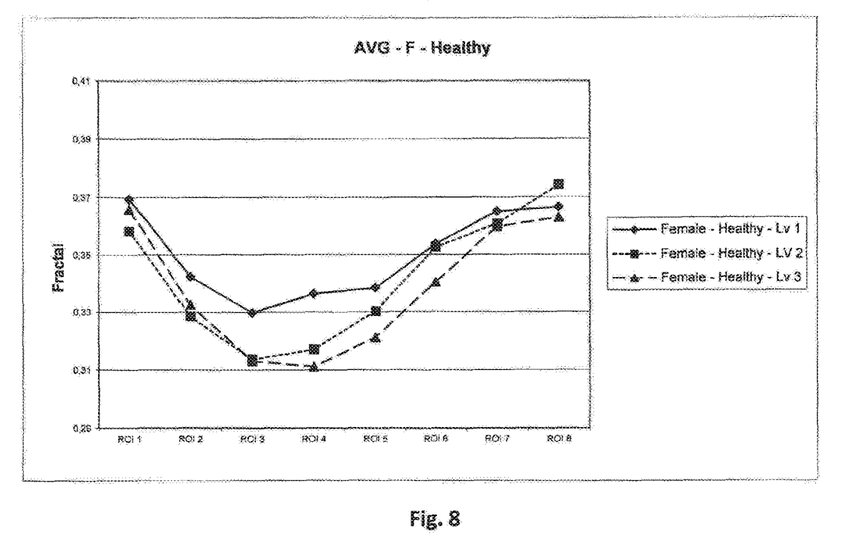
FIG. 8 shows a graph of a bone structure value for women found healthy.
Figure 9:
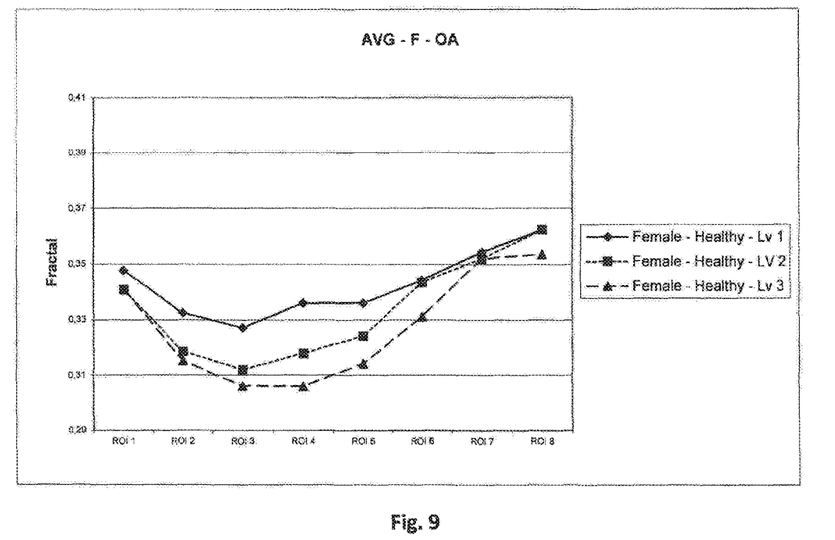
FIG. 9 shows a graph of a bone structure value for women having OA.

A full evaluation of the analysis grid—8×3 regions of interest were chosen in the example below, i.e. eight ROIs in transverse direction in 3 planes—provides the following result using 4 rotations:

FIG. 8: progression for women found healthy (N=80)
FIG. 9: progression for women having OA (N=62)

Comparison of the two diagrams reveals that the BSV is generally higher for healthy women than for those affected by OA. With healthy women, the BSV values decrease relatively quicker from ROI1 to ROI4 (about 15%) as compared to those suffering from OA (about 10%). Moreover, spreading of the BSV values from several analysis layers (Lv1 to Lv3) is larger due to the influence of epiphyseal development. Healthy women have about the same level of BSV values in ROI1 and ROI8. In women suffering from OA, these values decrease very strongly on a medial level and are about 4-5% below the lateral values.

Similar connections and relations of the BSV may be shown with respect to age, sex, ethnicity, BMI (body mass index) and other anthropometric data. A correlation between the development of osteoporosis and osteoarthritis could also be derived. Further, there is a connection between joint space height (or area) and the BSV. With such evaluations and the observation of progression, the advantage of an exact, reproducible joint space measurement according to this application also takes effect.

Using these findings, one may make improved predictions on the occurrence and development of bone joint diseases such as OA and OP.

In addition to determining the bone microarchitecture, detection of the joint space is also relevant for the assessment of joint diseases such as osteoarthritis or rheumatoid arthritis. The diagnostic value concerning the overall bone condition is increased, early detection and time course analyses are improved and the fracture risk can be determined more accurately.

The following steps are performed to said end:
recognising or generating the contours of the bone heads of the joint;
marking vertices of the bone heads;
defining at least one measurement range covering the joint space between the marked vertices, which has a width smaller than the joint head width and dimensions related to the joint head width;
measuring the joint space area within the at least one measurement range;
determining the ratio of the area of the at least one measurement range and the joint space area present within the at least one measurement range.

Figure 3:
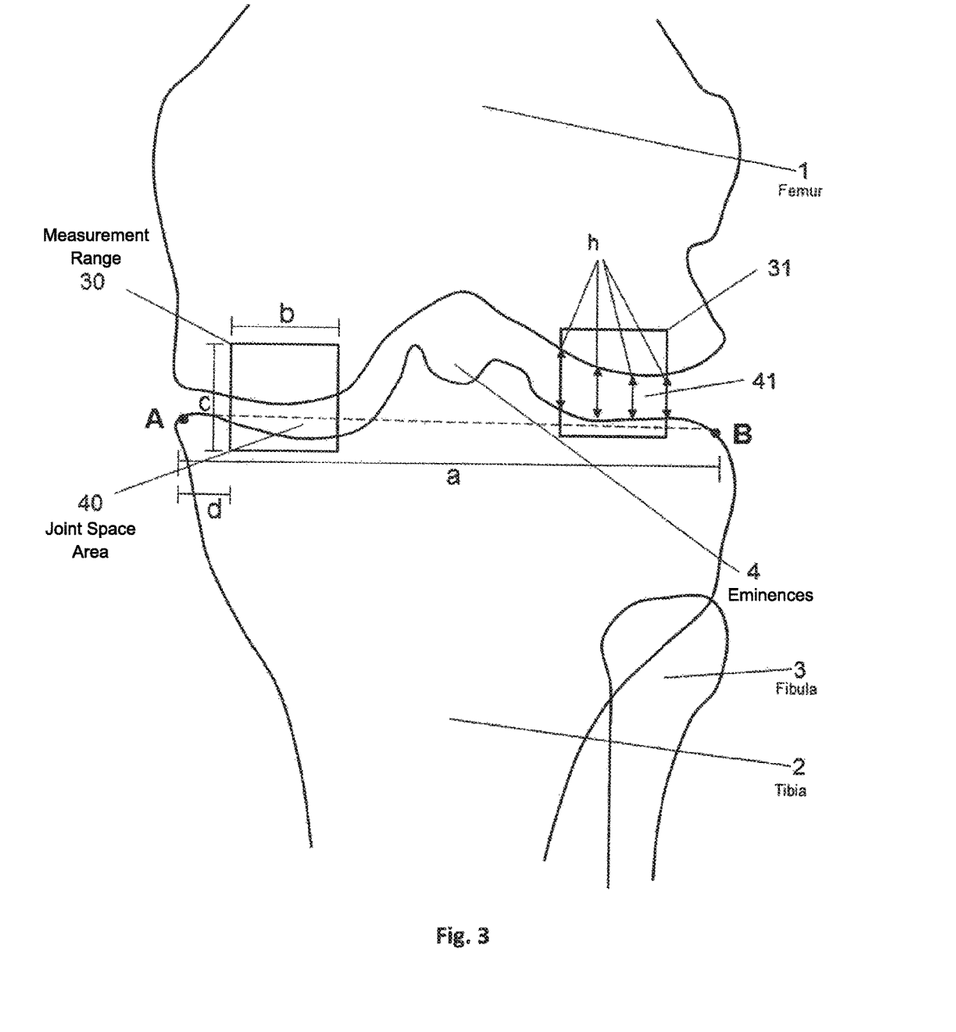
FIG. 3 shows a schematic rear view of a radiograph of a knee joint with two added measurement ranges for executing an embodiment of the method according to the invention.

FIG. 3 shows a schematic representation of a radiograph, in which the contours of the joint heads are visible.

Two measurement ranges 30, 31 whose size is related to anatomically set distances are selected. The measurement ranges 30, 31 are placed above the joint space in certain areas to determine the joint space area instead of only the height.

To be able to achieve this, it is necessary to know the position of the bone contours. The ratio of the overall measurement range area and the joint space area measured provides a value that quite accurately reflects the joint space and reacts very sensitively to changes in the case of repeated measurements. In addition, the minimum height in the joint space is determined and indicated.

In order to reproduce this measurement accuracy during the recording as well, a fixed knee positioning as in FIG. 1 is chosen. It provides for the knee being fixated in an adjustable manner for the recordings, resulting in unprecedented accuracy and reproducibility.

The developed analysis of the joint space area is based on the finding that previous methods in the knee joint and other joints (finger joints) are in great need of improvement. They use manually added distances between the bone heads. Manual inaccuracies, poor and inconsistent recording positions and/or inadequate image qualities are largely disregarded.

The method according to the invention improves the analysis in exactly these respects and others.

During the recording, the respective region of the body is supposed to be fixated in a repeatable manner. This defines the perspective of the recording permanently. For example, the knee recording (FIG. 3) must always be made in one direction, preferably in back-to-front direction as shown in FIG. 1.

The image quality is secured by set requirements and the distance measurement extended to become an area measurement. This is only possible if information on the bone contour positions is available. If it is, the joint space area in certain regions of the joint space can be determined. Typically, one will take those regions passed through by the main load.

In order to make the measurements comparable for different joint sizes, geometrical elements are used as measurement ranges, the sizes of which depend on set anatomical dimensions. In addition, the ratio of the area of the geometrical elements and the joint space areas is formed. This reveals an area quotient that is between zero and one and therefore remains comparable and lucid. Measurement of the joint space as an area increases the sensitivity and accuracy of the procedure. The actual benefit of this method results from a progress control function. Starting from the second measurement, the current values are supposed to be compared to the previous values and the percent change documented. As a reference, the first and the next to last measurement are always used.

The method of calculating the joint space, described based on the knee joint shown in FIG. 1 and FIG. 3, begins by recognising the contours of the knee bone heads, the femur and the tibia, on the radiograph. The vertices of the tibial plateau edges are marked as points A, B. Compared to the distance between the marks A, B, the measurement ranges 30, 31 are then placed over the medial (in FIG. 3 on the left) and lateral joint spaces (??? FIG. 3 on the right) in the form of rectangles.

The rectangular (typically square) measurement ranges 30, 31 have edge lengths b, c of 5 to 45% of the tibial head width a. Further, the measurement ranges 30, 31 are subjected to a lateral indentation d of 2 to 15%.

The preferred numerical ranges mentioned above may vary in the invention and depending on the type of joint. The measurement ranges 30, 31 may also assume a different geometrical shape.

The heights h between the femur 1 and the tibia 2 are measured within the measurement ranges 30, 31. The actual measurement, however, results from the ratio of the entire rectangular area b×c and the joint space area 40 (hatched) within the respective rectangles 30, 31.

The medial and lateral area quotients of the area are thus determined from the medial and lateral joint spaces 40, 41 between tibia 1 and femur 2 and the surrounding measurement ranges 30, 31, the width of the measurement ranges being between 5% and 45% of the tibial width and an indentation by 2 to 15% of the tibial width being made on both sides.

In addition, as mentioned above, the heights h of the medial or lateral joint space between tibia 1 and femur 2 are determined at several sites in a lateral and medial measurement ranges 30, 31, the width of which is between 5% and 45% of the tibial width and has an indentation by 2 to 15% of the tibial width on both sides.

Altogether, an evaluated combination of values of the fractal dimension from various analysis grid areas, the joint space heights and the quotients of the joint space area is used to assess the joint disease condition.

In order to achieve this, examinations were made with the goal to find out which areas contribute the most to a distinction between healthy and diseased. Bone structure values and also some joint space heights were combined to see which combination is most likely to divide the examined group of patients into healthy ones and diseased ones. It has been clearly shown that an integration of joint space heights raises the distinctive accuracy considerably. Also, particularly important image areas could be determined for the bone structure value measurement.

Figure 4:
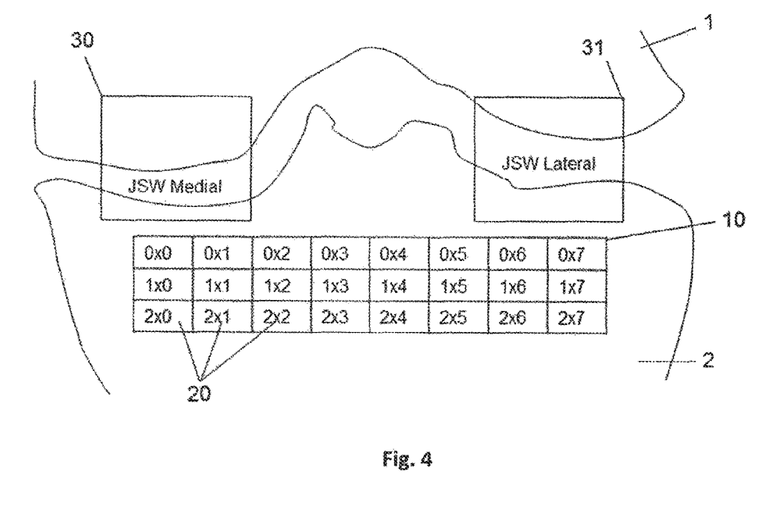
FIG. 4 shows a schematic rear view of a radiograph of a knee joint with an added analysis grid and added measurement ranges for executing another embodiment of the method according to the invention.

Based on a tested group of patients, the evaluation matrix could be filled according to the embodiment of the inventive method shown in FIG. 4.

An analysis grid of 3×8 image regions 20 was used. The analysis grid has a height of 30%, a width of 70% of the tibial width and a distance from the deepest contours of 8 mm. The rectangular joint space measurement ranges were selected with edge lengths of 20% of the tibial width and a lateral indentation of 5%.

The area quotients of the joint space measurement proved highly diagnostic with 95% for medial and 85% for lateral. The image regions 20 of the BSV measurement exhibited very different significances for the assessment.

Exhibiting 90%, the most important image region 20 is the one with the line and column numbers 0×0 (FIG. 4, top left). The image regions 20 in the top line were the most important with significances of 75 to 90%. The medium line had significances of 70 to 80% and the image regions 20 of the lowest line showed significances of 55 to 80%.

What is claimed is:

1. A method of x-ray analysis of bone joints comprising:
   recording a digital radiograph of a bone in an area of at least one of a joint head, socket;
   determining a fractal dimension of at least one image region;
   calculating, based on said fractal dimension of said at least one image region, a bone structure value;
   analysing multiple image regions;
   dividing the digital radiograph into multiple grid areas by an analysis grid, each of the multiple grid areas forming one of the image regions arranged in matrix form, the analysis grid comprising at least one line and at least two columns, the fractal dimension for each grid area determined pixel line by pixel line based on grey levels of image pixels contained therein, selected grid areas being used to assess a joint disease condition; and
   determining, using a processing device, progression of the fractal dimension in array elements, thereby enabling determination of a profile of the fractal dimension over a cross section.

2. The method of claim 1, wherein, to generate a mean value, the analysis grid is rotated around an angle α n times until a 360° rotation is achieved and the fractal dimension is calculated after each rotation.

3. The method of claim 1, wherein the analysis grid is selected to have 1 to 3 lines and 1 to 8 columns.

4. The method of claim 1, wherein a fractal profile is determined as a radial distribution of a fractal dimension of a grid line.

5. The method of claim 1, wherein the analysis grid is arranged in an area of a tibial head in the recorded digital radiograph, with the full width of the analysis grid equalling 60 to 100% of a width of a tibial plateau, a full height of the analysis grid being from 5% to 60% of the width of the tibial plateau, and a top edge of the analysis grid being arranged between 0 and 20 mm below a cortical bone of the tibial plateau depicted in the digital radiograph.

6. The method of claim 5, wherein the analysis grid is arranged symmetrically with respect to a central axis of a tibia depicted in the radiograph and parallel to a medial and lateral tibial plateau depicted in the digital radiograph.

7. The method of claim 1, wherein, in order to determine joint disease condition, an assessment of a joint space is further conducted by measuring a joint space area.

8. The method of claim 7, further comprising:
   recognising or generating contours of bone heads of a joint;
   marking vertices of the bone heads;
   defining at least one measurement range covering a joint space between marked vertices, which that has a width smaller than a joint head width and dimensions related to the joint head width;
   measuring a joint space area within the at least one measurement range; and
   determining a ratio of an area of the at least one measurement range and the joint space area present within the at least one measurement range.

9. The method of claim 8, wherein a medial and lateral area quotient of area from medial and lateral joint spaces between tibia and femur and surrounding measurement ranges is determined to assess the joint space of a knee joint, width of the measurement ranges being between 5% and 45% of the tibial width and an indentation of 2 to 15% being made on both sides of the tibial width.

10. The method of claim 9, wherein the heights of the medial or lateral joint space between tibia and femur are determined at multiple sites within a lateral and a medial measurement range, respectively, being between 5% and 45% of the tibial width and having an indentation of 2 to 15% on both sides of the tibial width.

11. The method of claim 1, wherein an evaluated combination of values of the fractal dimension from various analysis grid areas, the joint space heights and the quotients of the joint space area is used to assess joint disease condition.

* * * * *

UNITED STATES PATENT AND TRADEMARK OFFICE
CERTIFICATE OF CORRECTION

PATENT NO. : 9,968,322 B2  
APPLICATION NO. : 15/038006  
DATED : May 15, 2018  
INVENTOR(S) : Christian Schoen Page 1 of 1

It is certified that error appears in the above-identified patent and that said Letters Patent is hereby corrected as shown below:

On the Title Page

Item [72], should read:  
Davul Ljuhar, Wien (AT), Richard Ljuhar, Wien (AT)

In the Claims

Column 12, Line 25 Claim 8:  
Delete "...which that has"  
Insert --that has--

Signed and Sealed this  
Seventh Day of January, 2020

Andrei Iancu  
*Director of the United States Patent and Trademark Office*

UNITED STATES PATENT AND TRADEMARK OFFICE
CERTIFICATE OF CORRECTION

PATENT NO. : 9,968,322 B2
APPLICATION NO. : 15/038006
DATED : May 15, 2018
INVENTOR(S) : Schoen Page 1 of 1

It is certified that error appears in the above-identified patent and that said Letters Patent is hereby corrected as shown below:

This certificate supersedes the Certificate of Correction issued January 7, 2020. The certificate was issued prematurely and is vacated since the Petition to Correct Inventorship under CFR 1.324 dated October 1, 2019 was not acted on by Supervisory Patent Examiner in the Technology Center. The Certificate of Correction dated January 7, 2020, was published in error and should not have been issued for this patent.

Signed and Sealed this
Third Day of March, 2020

Andrei Iancu
*Director of the United States Patent and Trademark Office*

UNITED STATES PATENT AND TRADEMARK OFFICE
CERTIFICATE OF CORRECTION

PATENT NO. : 9,968,322 B2  
APPLICATION NO. : 15/038006  
DATED : May 15, 2018  
INVENTOR(S) : Christian Schoen Page 1 of 1

It is certified that error appears in the above-identified patent and that said Letters Patent is hereby corrected as shown below:

On the Title Page

Item [72], should read:  
Davul Ljuhar, Wien (AT), Richard Ljuhar, Wien (AT)

In the Claims

Column 12, Line 25 Claim 8:  
Delete "...which that has"  
Insert --that has--

Signed and Sealed this  
Fourteenth Day of April, 2020

Andrei Iancu  
*Director of the United States Patent and Trademark Office*